United States Patent [19]

Poppendiek et al.

[11] Patent Number: 4,832,042

[45] Date of Patent: May 23, 1989

[54] VENTILATOR HOOD SYSTEM FOR INDIRECT CALORIMETRY

[75] Inventors: Heinz F. Poppendiek, La Jolla; Cullen M. Sabin, Solana Beach, both of Calif.; Steven B. Heymsfield, New York, N.Y.

[73] Assignee: Emory University, Atlanta, Ga.

[21] Appl. No.: 86,844

[22] Filed: Aug. 19, 1987

[51] Int. Cl.$^4$ ............................................. A61B 5/08
[52] U.S. Cl. .............................. 128/730; 128/205.26; 128/205.19
[58] Field of Search .............. 128/716, 719, 727, 730, 128/201.23, 201.25, 205.26, 205.19, 205.25

[56] References Cited

U.S. PATENT DOCUMENTS

| | | | |
|---|---|---|---|
| 2,418,473 | 4/1947 | Lambertsen et al. | 128/205.26 |
| 3,552,391 | 1/1971 | Deaton | 128/205.26 |
| 4,181,129 | 1/1980 | Cameto et al. | 128/205.26 |
| 4,407,280 | 10/1983 | Trammell et al. | 128/205.26 |
| 4,444,183 | 4/1984 | Heckendorn | 128/205.26 |
| 4,651,727 | 3/1987 | Howorth | 128/201.23 |

FOREIGN PATENT DOCUMENTS 1179645  5/1959  France ............................. 128/717

Primary Examiner—Kyle L. Howell
Assistant Examiner—Angela D. Sykes
Attorney, Agent, or Firm—Frank E. Mauritz

[57] ABSTRACT

Ventilator hood systems for metabolic studies involving a study of the gases exhaled by a person uses suction to induce a flow of gases through a special hood construction which is loosely fitted over the head of the person when he is supported on his back and which serves to conduct a mixture of such exhaled gases and induced gases to suitable analyzing equipment without loss or eddying of the exhaled gases.

4 Claims, 2 Drawing Sheets

VENTILATOR HOOD SYSTEM FOR INDIRECT CALORIMETRY

TECHNICAL FIELD

The present invention relates to means and techniques useful in ventilator hood systems for indirect calorimetry.

BRIEF SUMMARY AND OBJECTS OF THE INVENTION

An object of the present invention is to provide improved means and techniques useful in measuring or determining the concentration and corresponding flow rates of gases being exhaled by a human being.

Another object of the present invention is to provide an improved system of this character in which a person resting in a horizontal position on his back has a loose fitting hood positioned over his head and suction means are applied to a discharge tube of the hood to induce a gas flow over the person's head and then into the discharge tube.

Another object of the present invention is to provide an improved loose fitting hood construction for these purpose wherein the suction applied thereto through its discharge tube may be large and the hood is completely open and shaped with respect to the person's head such that none of the exhaled gases from the person's nose and mouth can leak out of the hood other than through the discharge tube to which suction is being applied.

Still another object of the present invention is to provide an improved system of this character in which the flow of gases through the hood is smooth and direct and free of eddy currents and with assurance that all gases exhaled through the person's nose and mouth flow directly into the discharge tube to which suction is being applied.

Features of the invention which are believed to be novel are set forth in the appended claims. The invention itself, both as to its organization and manner of operation together with further objects the advantages thereof, may be best understood by reference to the following description taken in connection with the accompanying drawings in which:

BRIEF DESCRIPTION OF THE DRAWINGS

FIG. 5 is a view of the bottom side of the hood system shown in FIG. 1 with the person's head spaced therein to allow flow of gases into the hood as indicated by the arrows.

FIG. 6 is a sectional view taken on the line 6—6 in FIG. 2 and illustrates the manner in which edges of the transparent plastic hood are stiffened to assure rigidity of its illustrated shape.

Figure 1:
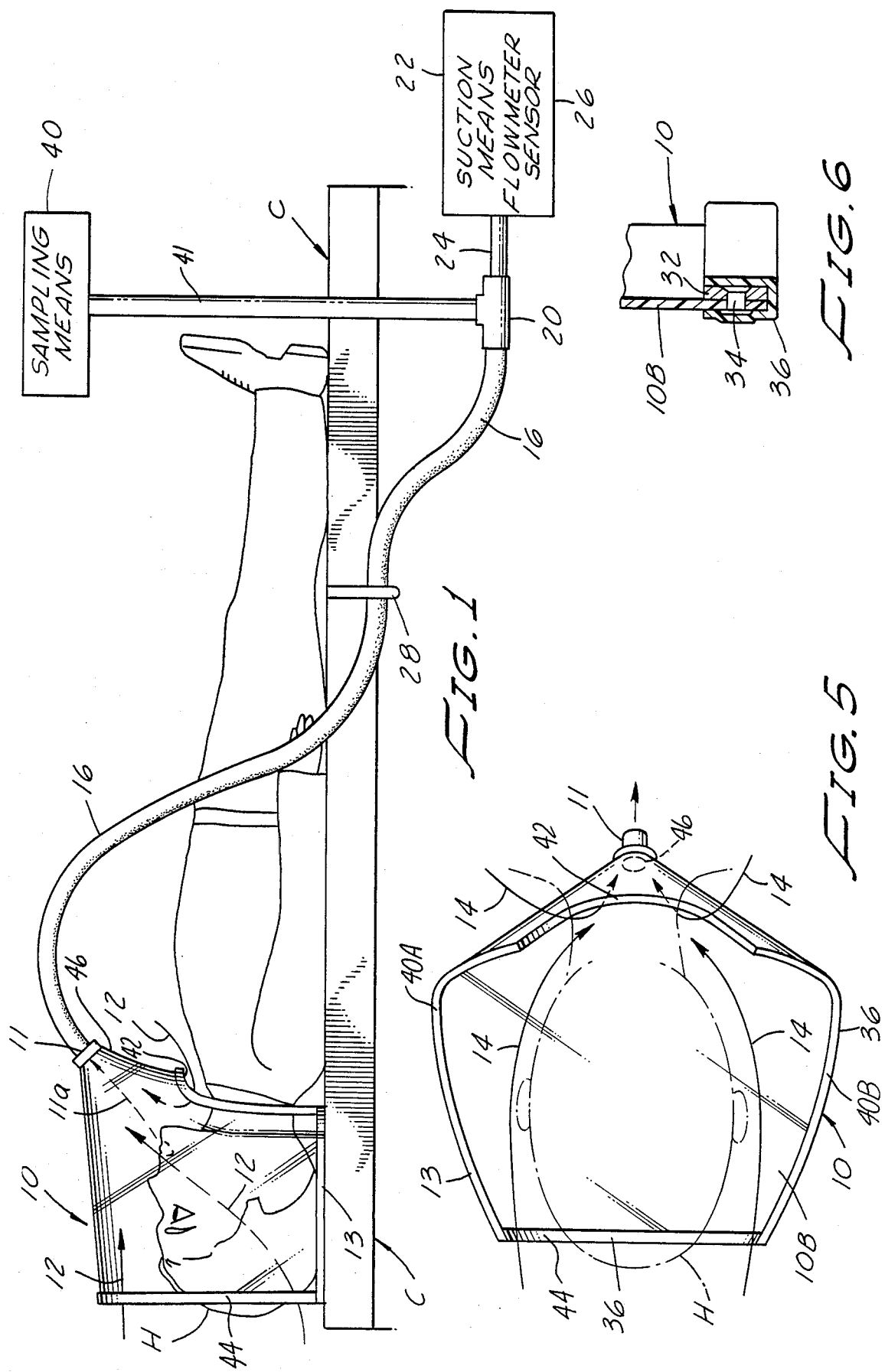
FIG. 1 illustrates a system embodying the present invention in relation to a person resting in a horizontal position on his back on a cot with his head within a hood system into which there is a flow of gases as indicated by the arrows.
Figure 2:
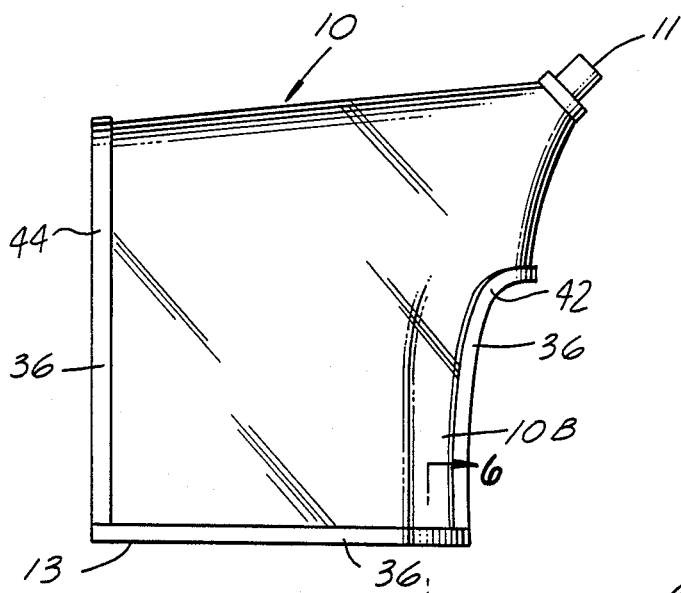
FIGS. 2, 3 and 4 illustrate constructional features of the hood system shown in FIG. 1, FIG. 2 being a side view, FIG. 3 being a front view and FIG. 4 being a rear view.
Figure 3:
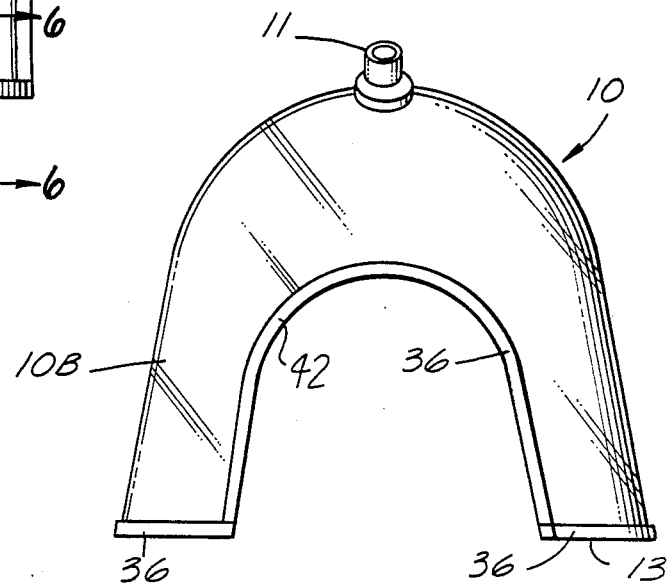

It is contemplated that measurements or determinations for indirect calorimetry be performed with the novel hood system 10 positioned over a person's head H while he or she rests in a horizontal position on a suitable support, for example a cot C as illustrated in FIG. 1.

The hood system 10 is constructed as illustrated in FIGS. 2-6 and is supported by the cot C upon which it rests so as to encompass the person's head and to allow the flow of gases into the hood through the open space between the hood and the person's head as indicated by three arrows 12 in FIG. 1 and four arrows 14 in FIG. 5. These arrows indicate direction of gas flow. These entering gases and also the gases exhaled through the person's nose and mouth flow into the discharge tube 16 which is connected to the hood outlet 11 and to which a vacuum is applied for inducing such directional gas flow. The hood outlet 11 is at a stategic location. As seen the outlet 11 is located uppermost and forwardmost on the hood with the axis of the outlet, as indicated by the dotted line 11A in FIG. 1 extending into the general vicinity of the person's mouth and nose with the flat planar base portion 13 of the hood resting on a flat surface of the cot or the flat surface of a mattress on the cot or a bed.

Suction is applied to hose 16 via a Tee connection 20 by suction producing means 22 which has associated conventional means in the form of a flowmeter sensor 26 for measuring the rate of gas flow in the connection 24 between the Tee connector 20 and suction producing means 22. The flow rate through the hood system 10 may be adjusted for a flow rate of approximately 50 liters per second by using a conventional flow rate adjustment (not shown) associated with the suction means 22 that produces such flow.

The sampling means 40 may be conventional and is connected to an outlet of the Tee connection via hose 41.

The apparatus functions to develope data for determining the concentrations and corresponding flow rates of gases being exhaled by a human being.

For these purposes the loose fitting hood is placed over a person's head while lying flat on his or her back as illustrated in the various figures. Gases of known concentrations are sucked into the hood in paths around the person's head to sustain the person's breathing operations. The composition and amounts of gases exhaled contain valuable information and all, together with all other gases entering the hood system enter the large tube 16 for evaluation as to flow rate by conventional flowmeter sensing means 26 and also as to composition in conventional sampling means 40, Important data is obtained with knowledge of the composition of the entering gases. None of the exhaled gases can leak out of the hood.

An advantage of this system involving an open-ended hood is that in the event of pump failure there is enough of an opening at one end so that carbon dioxide build-up does not reach a dangerous level and cause asphyxiation. This is assured by making the inlet end of the hood completely open and not unduly restricting the flow of incoming gases due to restricted gas passageway between the hood and the person's head. For these reasons the suction produced by the suction means 22 is required to be large. On the other hand, the suction should not be so large as to produce undue dilution of the exhaled gases with the gases entering the hood.

The sampling means 40 is commercially available and may be of the type marketed by Beckman Instruments for establishing valuable information such as, for example, quantities of oxygen, carbon dioxide and water vapor in establishing metabolic balance and metabolic rate of the person under study.

Conventional means in the form of a U-bolt 28 may be used to support the hose 16 on the frame of the cot.

The hood system 10 may be made of a suitable transparent plastic material such as, for example, a flat polycarbonate material having an 0.04 inch thickness. Its edges may be reinforced for wear and shape preserving purposes usig a construction exemplified in FIG. 6 wherein the plastic hood material 10B is stiffened by a flexible metal strip 32 that is secured thereto by, for example a rivet 34 and the edge thus stiffened may have a U-shaped plastic strip 36 secured around the assembly by suitable means, for example, glue for protective purposes.

SALIENT FEATURES OF INVENTION

Figure 4:
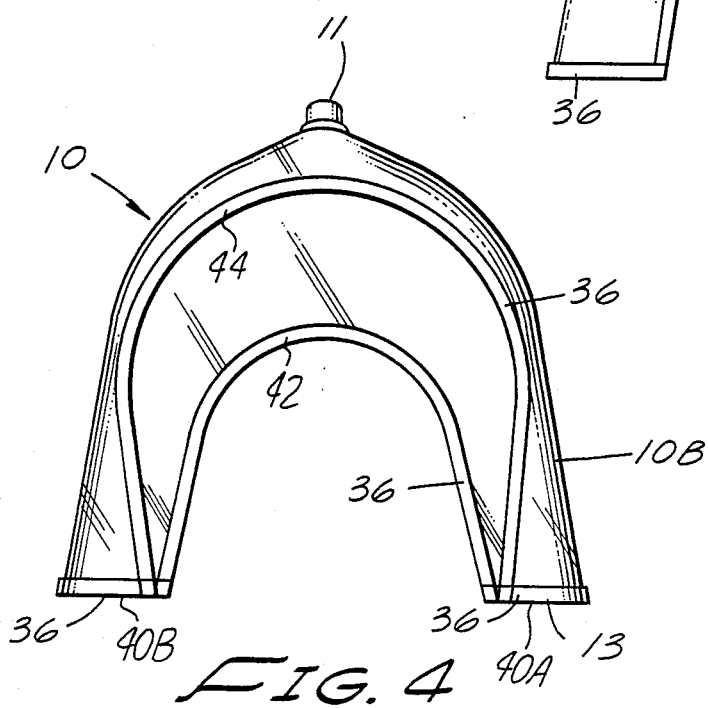

It will be seen that the hood structure illustrated in the drawings embodies a combination of salient features some of which are now enumerated. It has a planar base portion defined by spaced portions 40a, 40b as seen in FIGS. 4 and 5; a forward arcuate portion 42 which fits closely around the person's neck but in spaced relationship to it to allow free entry of gases as indicated by the arrow 12 in FIG. 1 and arrows 14 in FIG. 5; a larger rear arcuate portion 44 which fits closely around the person's head but in spaced relationship to allow free entry of gases as indicated by arrows 12 in FIG. 1 and arrows 14 in FIG. 5.; and of particular importance is the shape, location and orientation of the upper forwardly extending conical portion 46 with respect to the arcuate portions 42,44 and with respect to the nose and mouth of the person under the hood.

It is noted the general axis of such conical portion 46 represented by the dotted line 11a (FIG. 1) is inclined and directed to the general area of the person's nostrils and mouth for direct transit of exhaled gases into bottom opening 11 of such conical portion 46. The hood is transparent as disclosed to allow observation of the person's head and face at all times.

While particular embodiments of the invention have been shown and described, it will be obvious to those skilled in the art that changes and modifications may be made without departing from the invention in its broader aspects and therefor the aim in the appended claims is to cover all such changes and modifications as fall within the true spirit and scope of the invention.

We claim:

1. In a ventilator hood system wherein exhaled gases of a person are collected, a hood structure of rigid self-supporting material having a substantially planar base portion for resting on a flat surface, said structure having an integrally formed forward upwardly extending arcuate portion for loosely fitting around the person's neck without touching it to allow gases to be sucked into and through a first space between such arcuate portion and the person's neck, said structure having an integrally formed rear upwardly extending arcuate portion for loosely fitting around the person's head without touching it to allow gases to be sucked into and through a second space between said rear arcuate portion and the person's head, said structure having an integrally formed generally shaped conical outlet portion extending above and forwardly of said forward arcuate portion and having its axis inclined and extending in the general direction of the person's mouth and nostrils without touching the same when his head is within said hood, said conical portion having an outlet base portion into which the person's exhaled gases are directed together with gases that are sucked through said first and second spaces and into the interior of the hood structure.

2. The system as set forth in claim 1 of suction means applied to said outlet portion to induce a flow of gases through said first and said second spaces and through said outlet portion together with said exhaled gases.

3. The system as set forth in claim 1 in which said hood structure is of transparent material.

4. In a hood ventilator system wherein it is desired to collect gases exhaled by a person for examination, the method which consists in placing a rigid self-supporting hood structure loosely about and out of contact with the head of a person when he is being supported on his back to form a first forward opening between said structure and the person's neck and to form a second rear opening between said strueture and the person's head, applying suction to said hood structure to induce a flow of gases through both said first and second openings into said hood structure for breathing purposes, and using said suction to collect a mixture of said induced gases and said exhaled gases, said suction being applied to said hood structure at a region in said structure which is above the person's nostrils and is forward of the person's neck.

* * * * *